United States Patent
Persson

(10) Patent No.: US 7,166,128 B1
(45) Date of Patent: Jan. 23, 2007

(54) VOICE PROSTHESIS

(75) Inventor: Jan-Ove Persson, Hoor (SE)

(73) Assignee: Atos Medical AB, Hörby (SE)

( * ) Notice: Subject to any disclaimer, the term of this patent is extended or adjusted under 35 U.S.C. 154(b) by 0 days.

(21) Appl. No.: 09/171,889

(22) PCT Filed: May 26, 1997

(86) PCT No.: PCT/SE97/00855

§ 371 (c)(1),
(2), (4) Date: Aug. 30, 1999

(87) PCT Pub. No.: WO97/45075

PCT Pub. Date: Dec. 4, 1997

(30) Foreign Application Priority Data

May 24, 1996 (SE) ................................ 9601995

(51) Int. Cl.
*A61F 2/20* (2006.01)

(52) U.S. Cl. .......................................... 623/9
(58) Field of Classification Search ................ 623/2.1, 623/9
See application file for complete search history.

(56) References Cited

U.S. PATENT DOCUMENTS

| | | | | |
|---|---|---|---|---|
| 3,974,854 A | * | 8/1976 | Kurpanek | 623/2 |
| 4,979,955 A | * | 12/1990 | Smith | 623/2 |
| 5,064,433 A | * | 11/1991 | Blom | 623/9 |
| 5,135,538 A | * | 8/1992 | Pawlak | 623/2 |
| 5,314,470 A | | 5/1994 | Persson | |
| 5,391,205 A | * | 2/1995 | Knight | 623/9 |
| 5,632,775 A | * | 5/1997 | Suding | 623/9 |
| 5,693,097 A | * | 12/1997 | Laguette | 623/9 |
| 5,814,100 A | * | 9/1998 | Carpentier | 623/2 |
| 5,957,978 A | * | 9/1999 | Blom | 623/9 |

FOREIGN PATENT DOCUMENTS

NL     9311820     6/1993

* cited by examiner

*Primary Examiner*—Corrine McDermott
*Assistant Examiner*—William H Matthews

(57) ABSTRACT

A voice prosthesis to be mounted in a fistula between trachea and esophagus comprises a spool-shaped element with a through passage and a valve mechanism controlling the connection through said passage and having sealing surfaces which can be pressed against each other, means being provided to produce a magnet force acting between the sealing surfaces to keep said surfaces pressed against each other in the closed position of the valve mechanism.

10 Claims, 6 Drawing Sheets

VOICE PROSTHESIS

FIELD OF THE INVENTION

The invention relates to a voice prosthesis to be mounted in a fistula between trachea and esophagus, comprising a spool-shaped element having a through passage and a valve mechanism controlling the connection through said passage, said valve mechanism having sealing surfaces which can be pressed against each other.

BACKGROUND OF THE INVENTION

When a person's larynx has been removed by surgery due to pathological changes in the throat, the trachea is sutured to an opening in the throat (tracheostoma). By the surgery the person has lost the ability to speak, and in order to restore this ability a method has been applied for several years, in a voice prosthesis of the kind referred to above is mounted in a fistula, i.e. a passage between trachea and esophagus. At speech the tracheostoma is occluded by sealing the same either by the patient placing the fingers against the tracheostoma or by the tracheostoma being closed by an in connection therewith provided stoma valve. Then, the expiration air is pressed from the lungs through the voice prosthesis into esophagus where the mucous membranes of the throat are brought into vibration and speech is produced as a consequence thereof. Several voice prosthesis are described in U.S. Pat. No. 4,911,716, U.S. Pat. No. 4,435,853, U.S. Pat. No. 4,820,304, and DD-Al-275 183. The voice prosthesis is fixed in the fistula by means of two flanges on the spool-shaped element or by means of a flange and ribbons. The spool-shaped element can be cylindrical or oval and preferably it is made of silicon rubber. All existing voice prostheses have in common that they provide a check valve function, which means that the valve mechanism normally is closed but opens when air is pressed from trachea via the valve to esophagus. The valve mechanism is maintained in the closed position by spring bias which in most cases is maintained by elasticity of the material from which the voice prosthesis is made.

When existing voice prostheses are mounted in the fistula the function is acceptable initially but they have a non-acceptably short life ranging from a week up to two years. There are two reasons for this short life, viz.
1) Growth of fungus, candida, will cover the sealing surfaces of the valve mechanism, which causes leakage at the intake of beverages and is the primary reason for exchange of the voice prosthesis.
2) Fatigue of the spring bias (the material of the voice prosthesis) so that the valve as a consequence thereof will be partly open in the normal position causing leakage through the voice prosthesis.

A further drawback adds to these drawbacks viz. that the spring bias which shall maintain the valve mechanism closed in the normal position increases with the opening movement of the valve mechanism so that a considerably increased air resistance will be obtained as a consequence thereof at increased air flow, which means that the patient will be restrained from producing a more powerful speech or in any case cannot produce such speech without great effort, which makes the speech strenuous.

In existing voice prostheses the valve mechanism opens relatively quickly and preferably at low pressure when air with the stoma closed is pressed against the valve mechanism. Then, when the air flow is increased at speech the flow resistance will quickly be increased as mentioned above.

It is known per se to provide a valve mechanism with a permanent magnet function in order to maintain the valve mechanism in closed condition. Thus, there is disclosed in WO 93/11820 a cough valve having a valve flap which is kept in closed position against a seat by the force of a permanent magnet, such force acting between the valve flap and the seat, in order to be opened at a rising high overpressure in trachea such as at an attack of coughing. It is thus the question of a pure safety valve wherein the permanent magnet function is utilized for a completely other purpose than for overcoming the drawbacks connected with existing voice prostheses, which have been discussed above and which are not at all mentioned in WO 93/11820.

As mentioned above the growth of candida on the sealing surfaces of the voice prosthesis is the main reason for the necessity of exchanging the voice prosthesis. It is well known that the candida fungus affects silicon rubber which is the material almost exclusively used in voice prostheses, and above all at such places which are in contact with the mucous membranes in the throat.

SUMMARY OF THE INVENTION

The present invention provides a voice prosthesis comprising a spool-shaped hollow body for insertion into a fistula in a tracheoesophageal wall of a patient. Such body having an open tracheal end an open esophageal end. A first retention flange is disposed at the tracheal end of the body. A second retention flange is disposed at the esophageal end of the body. Such body defining a through passage between the tracheal end and the esophageal end. A valve seat is formed by the body at the esophageal end thereof. A valve flap cooperates with such valve seat to control air flow through the through passage of such body. The valve flap occludes air flow through such through passage in a closed position of the valve flap against the valve seat. A magnet is disposed on one of such valve flap and such valve seat. A magnetically attracted material is disposed on an opposed one of such valve flap and such valve seat. The magnet and the magnetically attracted material provide a magnet force between the valve flap and the valve seat in the closed position of the valve flap. Seating surfaces are formed by such valve flap and such valve seat, respectively, to be pressed against each other by a magnetic force in such closed position. The magnet force normally maintaining such valve flap in sealing engagement with the valve seat in such closed position to be disengaged therefrom by an overpressure in trachea overcoming such magnet force.

OBJECTS OF THE INVENTION

It is, therefore, one of the primary objects of the present invention to provide a voice prosthesis will utilize a higher initial pressure at speech in order to provide a reduced closing force with greater air flow once the valve mechanism has opened.

Another object of the present invention is to provide a voice prosthesis which is candida resistant.

These and various other objects and advantages of the present invention will become more readily apparent to those persons skilled in the art from the following more detailed description of the invention, particularly, when such description is taken in conjunction with the attached drawings.

BRIEF DESCRIPTION OF THE PRESENTLY PREFERRED AND VARIOUS ALTERNATIVE EMBODIMENTS OF THE INVENTION

For a better understanding of the present invention reference is now made more particularly to the drawings.

When the magnet function is utilized in order to maintain the voice prosthesis in closed position, as in the voice prosthesis according to the present invention, the portions sealing against each other in the valve mechanism can consist of, or be coated with, a hard candida resistant material, for example PVDE, polypropylene or polyethylene, which, however, in existing voice prostheses rather quickly would result in beginning leakage at beginning fatigue of the silicon rubber the elasticity of which produces the closing force, because an increased compression force is required in order to seal between two hard surfaces than between two soft surfaces. A reduced compression force cannot push away food surface thereof to be engaged with the seat is provided with a plate 19 of candida resistant material or is coated with such a material.

A permenent magnet 20 is provided in the valve flap and is connected with the flap by gluing or by being moulded into the material at injection moulding of the valve flap. Seat 15 should be made of a magnetically attractable material so that the valve flap by magnetic force normally is held in closed position sealingly engaging the seat but can be lifted momentarily from the seat by an overpressure in trachea overcoming the magnet force. Lining 14 or at least that part thereof which forms seat 15 preferably consists of magnetic stainless steel. In a modification of the embodiment shown the magnet or several magnets are provided in seat 15 and a plate 19 is made of a magnetically attractable material such as magnetic stainless steel. Shield 16 protects the valve mechanism against candida attack. In order that the permanent magnet 20 shall be protected against corrosion it can be coated with a corrosion resistant material.

Figure 2:
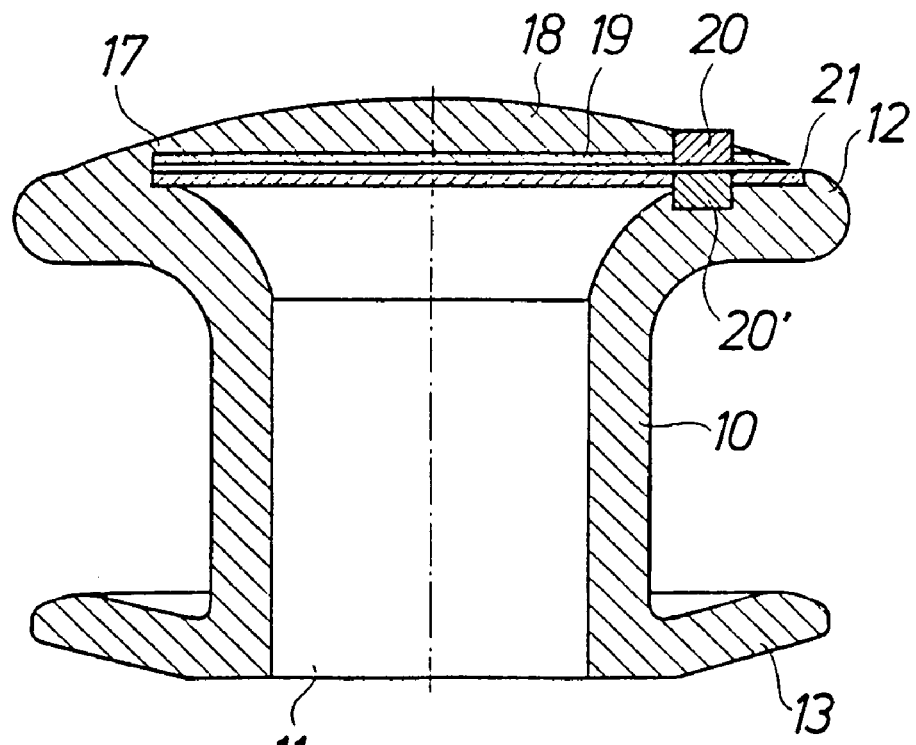
FIG. 2 is a side elevation view partially in cross-section illustrating another embodiment of the present invention.
Figure 3:
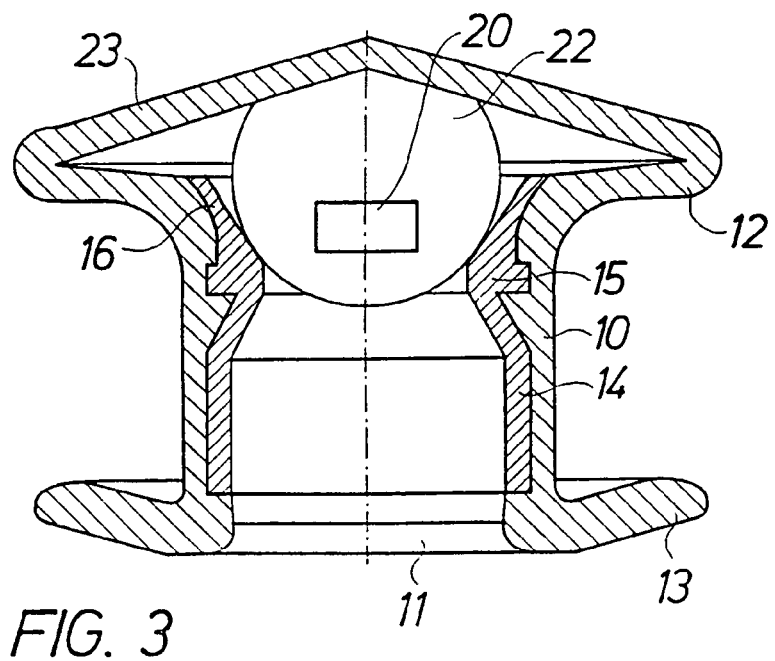
FIG. 3 is a side elevation view partially in cross-section illustrating still another embodiment of the present invention.

FIG. 2 discloses a modification of the embodiment in FIG. 3 wherein the seat comprises a flat ring 21. In this case valve flap 18 as well as seat ring 21 are provided with a permanent magnet 20 and 20', respectively. Alternatively, only either plate 19 on the valve flap or seat ring 21 is provided with magnet and the seat ring and the plate, respectively, is made of a magnetically attractable material.

Figure 1:
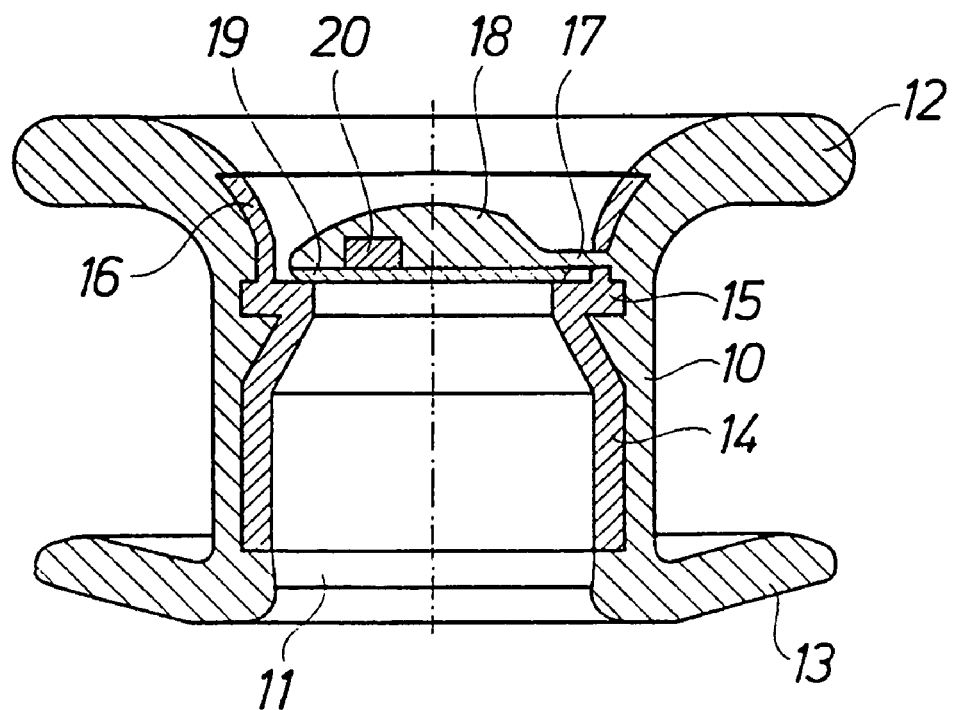
FIG. 1 is a side elevation view partially in cross-section illustrating one embodiment of the present invention.

The embodiment shown in FIG. 3 principally is constructed in the same way as the embodiment in FIG. 1 but valve flap 18 has been replaced by a valve element formed as a ball 22 which is supported by a strip 23 made integral with flange 12 and allowing ball 22 to be lifted from seat 15 under elastic yielding. Ball 22 is provided with one or more permanent magnets 20 in order to be held by magnet force in engagement with seat 15 consisting of a magnetically attractable material. Alternatively ball 22 in its entirety can comprise a permanent magnet, or one or more permanent magnets can be provided in the seat to attract ball 22 which in that case is made in its entirety of a magnetically attractable material.

Figure 4:
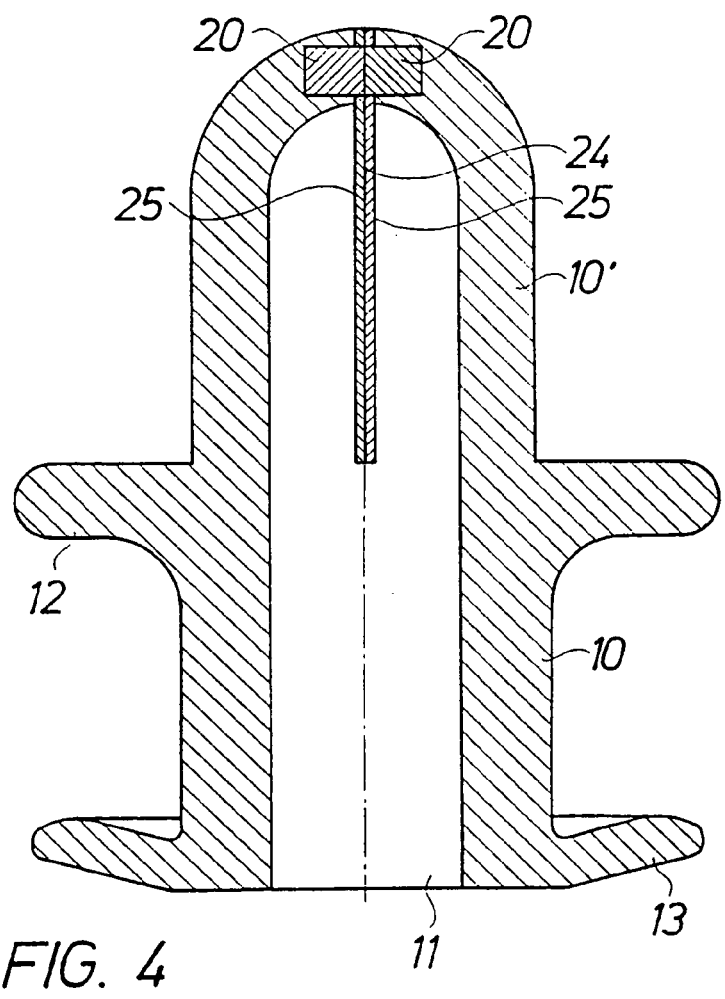
FIG. 4 is a side elevation view partially in cross-section illustrating yet another embodiment of the present invention.

The embodiment in FIG. 4 is slightly different from the embodiment previously described because the valve mechanism is of the type "duck bill". It is formed by a slotted extension 10' of the spool-shaped element 10, projecting from flange 12. The slot is indicated at 24 and is defined by surfaces having a coating 25 of candida resistant material. The two halves of extension 10' formed by the slot are mutually attracted by two permanent magnets 20 one on each of said two halves, in order that the slot, i.e. the valve mechanism shall be kept closed. At overpressure in trachea acting in passage 11 the magnet force will be overcome and slot 24 will be opened under elastic separation of the two halves of extension 10' so that a connection through passage 11 will be established. Instead of the two halves of extension 10' being provided with a magnet, only one of said halves can have a magnet and the other one can have a block of magnetically attractable material co-operating with the magnet.

Figure 5:
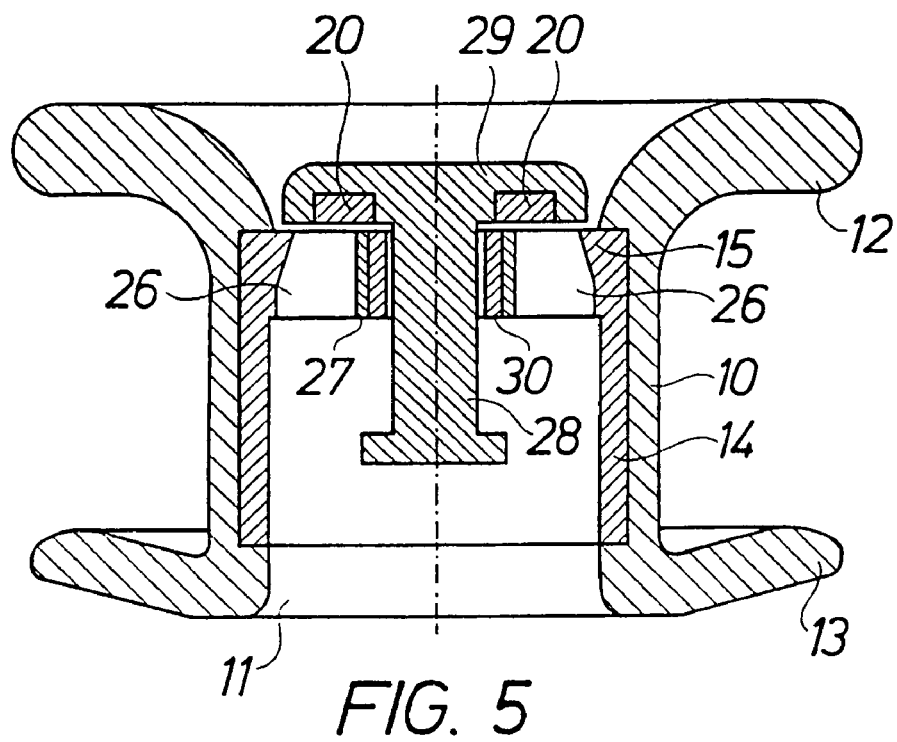
FIG. 5 is a side elevation view partially in cross-section illustrating a further embodiment of the present invention.

In the embodiment according to FIG. 5 lining 14 made of candida resistant material forms seat 15 in passage 11 said seat forming radial arms 26 supporting a guide 27 for a stem 28 on a disk valve 29 co-operating with seat 15. Disc valve 29 is provided with one or more permanent magnets 20, and for co-operation with the magnet or the magnets, respectively, guide 27 is partly made of a magnetically attractable material 30 so that disc valve 29 is kept in engagement with seat 15 by magnet force. At overpressure in passage 11 which acts against disc valve 29 this is lifted from seat 15 the magnet force being overcome, so that a connection is established through passage 11. In a modification of this embodiment the guide is provided with a permanent magnet and the disc valve is provided with or is made of a magnetically attractable material. Preferably, disc valve is made of a candida resistant material in its. entirety.

Figure 6:
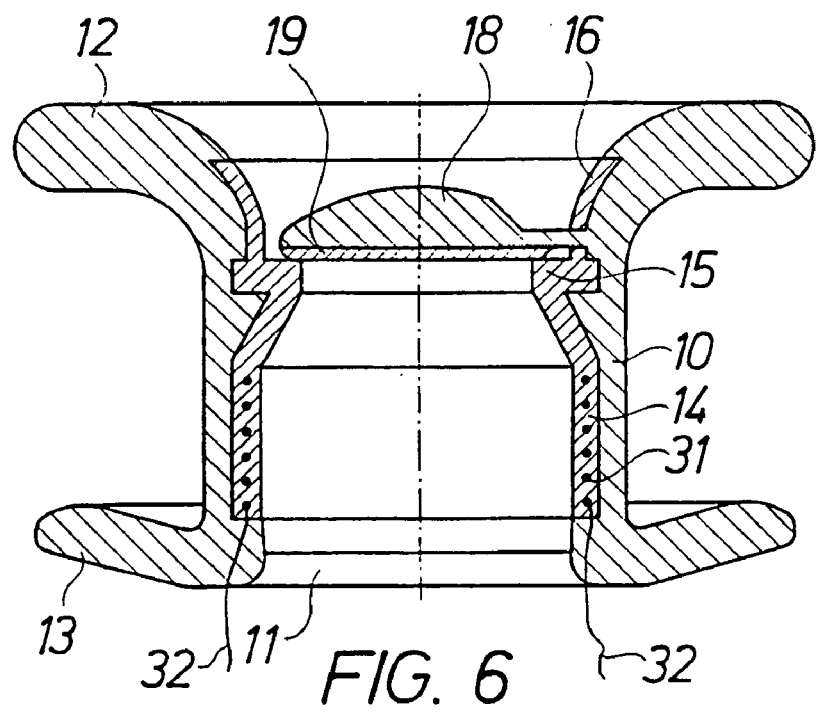
FIG. 6 is a side elevation view partially in cross-section illustrating an additional embodiment of the present invention.

FIG. 6 discloses an embodiment in accordance with FIG. 1 wherein the permanent magnet, however, is replaced by an electromagnet. A wire winding 31 is embedded into lining 14 and has connection wires 32 for connection of the winding to an electric power source. The lining and thus the seat in this case should consist of a magnetizable material to be magnetized at energization and thus attract plate 19 on valve flap 18 said plate consisting of a magnetically attractable material.

Figure 7:
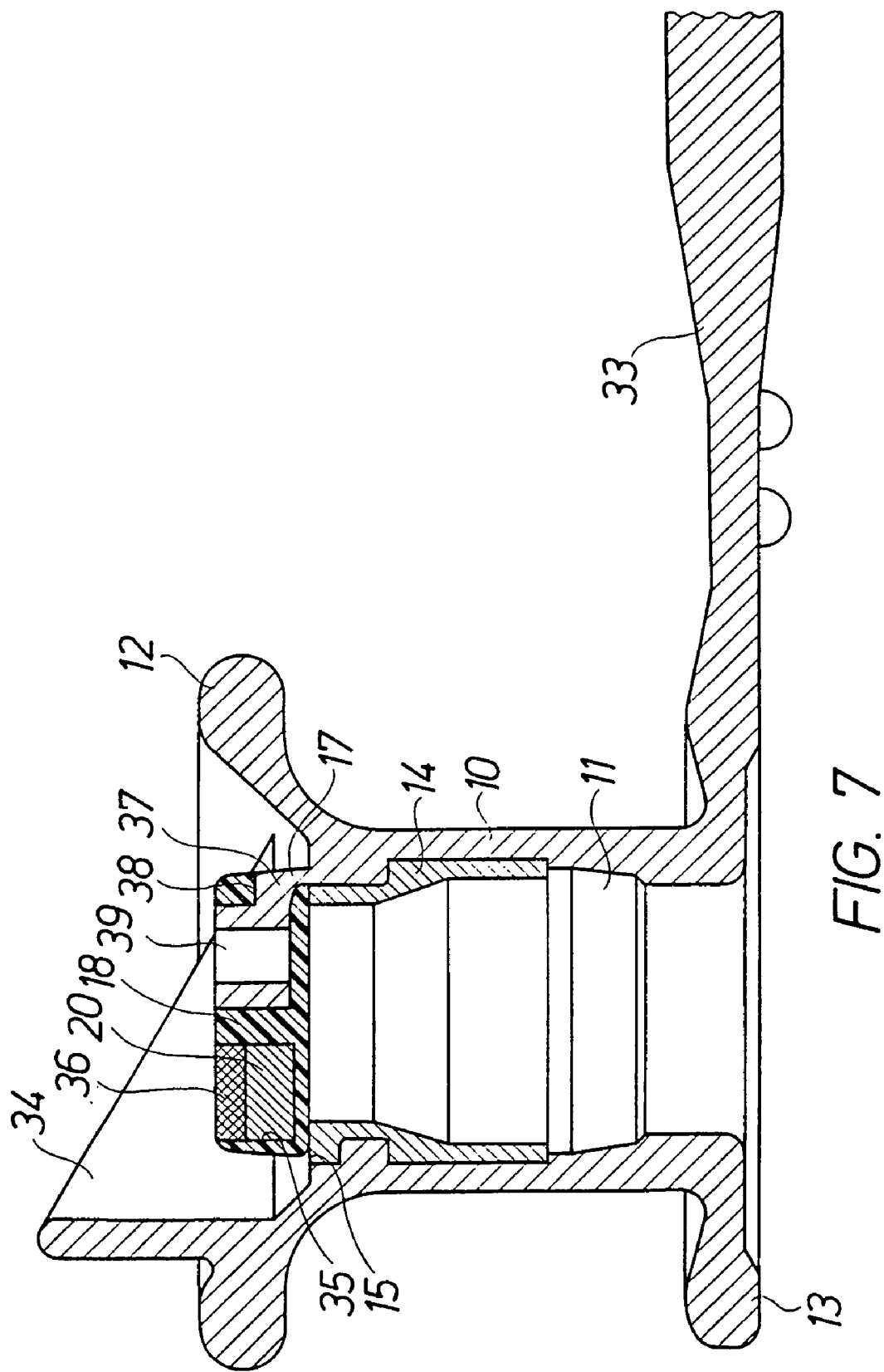
FIG. 7 is a side elevation view partially in cross-section illustrating a presently preferred embodiment of the present invention.

In FIG. 7 the embodiment of the voice prosthesis according to the invention presently preferred is disclosed said embodiment being a modification of the embodiment in FIG. 1 as is the embodiment in FIG. 2. In this embodiment the voice prosthesis comprises a spool-shaped element 10 of silicon rubber having a distal outside flange 12 and a proximal outside flange 13 said latter flange being shown with a "tail" or strap 33 (fragmentarily shown) having a suitable length. This strap can be used in handling the voice prosthesis when it shall be mounted in or demounted from the fistula and also can serve as anchoring means for anchoring the voice prosthesis on an insertion instrument. The spool-shaped element in this embodiment forms an obliquely bevelled extension 34 at the distal end. When the voice prosthesis is positioned in the fistula said portion extends into esophagus and prevents liquid and food passing down through esophagus from entering passage 11 in the spool-shaped element and from disturbing the function of the voice prosthesis. A lining 14 of a candida resistant and magnetically attractable material, e.g. magnetic stainless steel is inserted into the passage, and said lining at the distal end forms the annular seat 15 of the voice prosthesis. The lining can be attached by vulcanization or gluing to the spool-shaped element.

The valve flap 18 of the voice prosthesis, which cooperates with seat 15 consists of hard plastics and forms a cavity 35 in which a permanent magnet 20 is located and is retained therein by means of a glue layer 36 in the cavity, extending over the magnet. Valve flap 18 is articulately I connected with the spool-shaped element 10 by means of a portion 37 which is injection moulded integrally with the spool-shaped element in another cavity 38 in valve flap 18 and at a web 17 provided as a joint connects to the rest of element 10, a pin 39 on the valve flap being surrounded by; portion 37 for locking said portion on the valve flap.

In this embodiment the lining can be made of plastics and can have at the distal end thereof a permanent magnet moulded or glued into the lining. By this arrangement the risk of the lining eventually being magnetized by magnet 20 is avoided. By such magnetization the magnetic retainment of the valve flap in closed position may be uncontrollably strong and may require an opening pressure which is too high.

Figure 8:
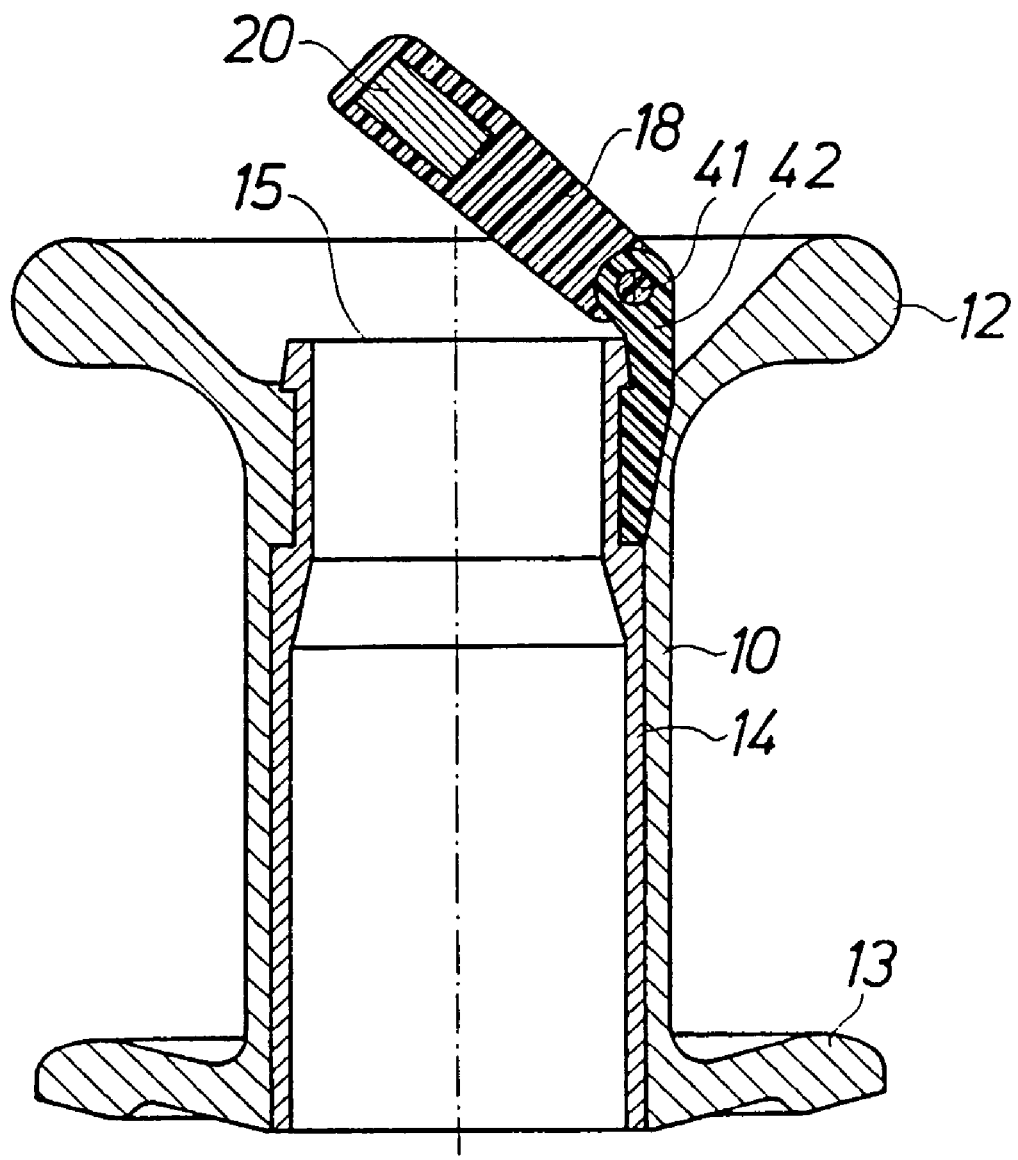
FIG. 8 is a side elevation view partially in cross-section illustrating another embodiment of the present invention.

In the embodiment according to FIG. 8 valve flap 18 consisting of hard plastics with a magnet 20 moulded there into is connected by means of a pivot 41 with a hinge flange 42 of hard plastics which is attached by vulcanization to the spool-shaped element and is kept engaged with the outside surface of lining 14 which can consist of a magnetically attractable material such as stainless steel, or can be made of plastics with a built-in permanent magnet for co-operation with magnet 20.

Figure 9:
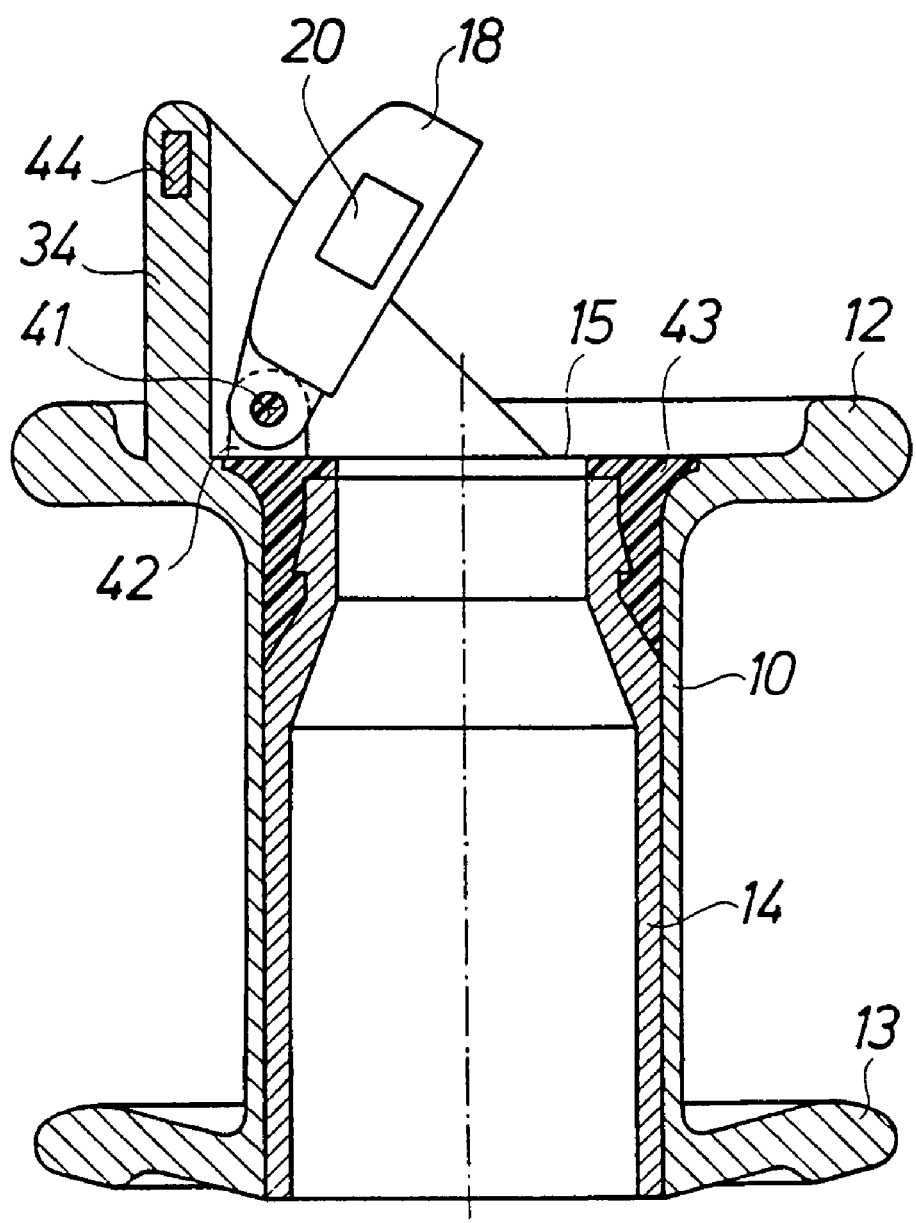
FIG. 9 is a side elevation view partially in cross-section illustrating still another embodiment of the present invention.

In FIG. 9 hinge flange 42 is made as an integral portion of a ring 43 of hard plastics, which forms seat 15 and is attached to the spool-shaped element 10 by vulcanization and which engages lining 14 inserted into said element.

Also in this case the lining can consist of stainless steel or plastics with a built-in permanent magnet in order to keep the valve flap against seat 15 in cooperation with magnet 20 moulded into the valve flap. The spool-shaped element in this case has an obliquely bevelled extension 34 with a permanent magnet 44 moulded there into, which has such polarity in relation to magnet 20 that it repels this magnet and thus the flap so that this cannot be left in open position.

Lining 14 in the several embodiments of the voice prosthesis according to the invention can be attached to he spool-shaped element 10 by vulcanization or gluing, but it is also possible to provide as an alternative or complement; a mechanical attachment by the lining being pushed into passage 11 and under elastic yielding of the spool-shaped element snaps into positive engagement with said element at shoulders on the outside surface of the lining and inside the passage.

Instead of the lining being made of stainless steel in the embodiments according to FIGS. 1 and 3 and 7 to 9 it can be made of hard plastics with one or more permanent magnets moulded thereinto for co-operation with the magnet in the valve flap.

I claim:

1. A voice prosthesis comprising:
   a spool-shaped hollow body for insertion into a fistula in a tracheoesophageal wall of a patient, said body having an open tracheal end an open esophageal end;
   a first retention flange at said tracheal end of said body;
   a second retention flange at said esophageal end of said body, said body defining a through passage between said tracheal end and said esophageal end;
   a valve seat formed by said body at said esophageal end thereof;
   a valve flap cooperating with said valve seat to control air flow through said through passage of said body, said valve flap occluding air flow through said through passage in a closed position of said valve flap against said valve seat;
   a permanently magnetically attracted material disposed on an opposed one of said valve flap and said valve seat, said magnet and said magnetically attracted material providing a magnet force between said valve flap and said valve seat in said closed position of said valve flap; and
   a permanent magnet on one of the valve flap and valve seat, providing a permanent magnetic force on said permanently magnetically attracted material;
   seating surfaces formed by said valve flap and said valve seat, respectively, to be pressed against each other by a magnetic force in said closed position, said magnet force normally maintaining said valve flap in sealing engagement with said valve seat in said closed position to be disengaged therefrom by an overpressure in trachea overcoming said magnet force.

2. A voice prosthesis, according to claim 1, wherein said at least one of said magnet and said magnetically attracted material is a permanent magnet.

3. A voice prosthesis, according to claim 2, wherein said magnet is a permanent magnet.

4. A voice prosthesis, according to claim 1, wherein said at least one of said magnet and said magnetically attracted material is an electromagnet.

5. A voice prosthesis, according to claim 4, wherein said magnet is an electromagnet.

6. A voice prosthesis, according to claim 1, wherein said at least one of said magnet and said magnetically attracted material are secured by gluing.

7. A voice prosthesis, according to claim 1, wherein said at least one of said magnet and said magnetically attracted material are secured by molding.

8. A voice prosthesis, according to claim 1, wherein said at least one of said magnet and said magnetically attracted material are coated with a surface layer of a corrosion resistant material.

9. A voice prosthesis, according to claim 1, wherein at least one of said sealing surfaces is a candida resistant material.

10. A voice prosthesis, according to claim 9, wherein one sealing surface of said candida resistant material is formed as a valve seat which extends axially on at least one side of said valve seat as a lining of said through passage in said spool-shaped hollow body.

* * * * *